(12) United States Patent
Euler

(10) Patent No.: US 7,835,789 B2
(45) Date of Patent: Nov. 16, 2010

(54) REFRACTORY PERIOD STIMULATION TO INCREASE VENTRICULAR PERFORMANCE

(75) Inventor: David E. Euler, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1150 days.

(21) Appl. No.: 11/379,904

(22) Filed: Apr. 24, 2006

(65) Prior Publication Data

US 2007/0250128 A1    Oct. 25, 2007

(51) Int. Cl.
*A61N 1/362* (2006.01)
(52) U.S. Cl. .......................................... 607/9
(58) Field of Classification Search ...................... 607/9
See application file for complete search history.

(56) References Cited

U.S. PATENT DOCUMENTS

| | | | |
|---|---|---|---|
| 5,213,098 A | 5/1993 | Bennett et al. | |
| 6,738,667 B2 | 5/2004 | Deno et al. | |
| 6,748,261 B1 * | 6/2004 | Kroll et al. | 600/510 |
| 7,142,916 B2 | 11/2006 | Deno et al. | |
| 7,184,833 B2 | 2/2007 | Ganion et al. | |
| 7,233,824 B2 | 6/2007 | Kleckner et al. | |
| 7,289,850 B2 | 10/2007 | Burnes et al. | |
| 7,292,888 B2 | 11/2007 | Deno et al. | |
| 7,515,958 B2 * | 4/2009 | Sheldon et al. | 607/9 |
| 2002/0183686 A1 * | 12/2002 | Darvish et al. | 604/21 |
| 2003/0023279 A1 | 1/2003 | Spinelli et al. | |
| 2004/0049235 A1 | 3/2004 | Deno et al. | |
| 2004/0220640 A1 | 11/2004 | Burnes et al. | |
| 2005/0038479 A1 * | 2/2005 | Deno et al. | 607/9 |

FOREIGN PATENT DOCUMENTS

| | | |
|---|---|---|
| WO | WO0130436 | 5/2001 |
| WO | WO2004080533 | 9/2004 |

* cited by examiner

*Primary Examiner*—Carl H Layno
*Assistant Examiner*—Brian T Gedeon
(74) *Attorney, Agent, or Firm*—Stephen W. Bauer; Reed A. Duthler

(57) ABSTRACT

Implantable pulse generators (IPGs) are adapted to deliver stimulation to refractory myocardial tissue. An IPG nominally delivers one to six monophasic stimulation pulses. Because monophasic stimulation tends to accumulate polarization, a programmable blanking period of between about 20 milliseconds (ms) and about 300 ms is implemented (subsequent to delivery of the last pulse in a RPS pulse train) to allow recovery from polarization. The stimulation pulse width is about 0.03 ms to about 1.6 ms and voltage amplitude of 0.5 volts to 8 volts at about 50 Hz. The amplitude of electrical current of the stimulation pulses is less than or equal to approximately 50 milliamps. The pulses are delivered to multiple sites within a cardiac chamber and device performance and/or diagnostic information can be stored within a memory structure and reviewed to confirm delivery of a desired therapy regimen.

8 Claims, 4 Drawing Sheets

REFRACTORY PERIOD STIMULATION TO INCREASE VENTRICULAR PERFORMANCE

CROSS REFERENCE TO RELATED APPLICATIONS

This patent disclosure relates to two co-pending non-provisional patent applications filed on even date hereof; namely, application Ser. No. 11/379,892 by Deno and Warkentin entitled, "A METHOD OF DELIVERYING PESP/ICC AS WELL AS ADJUSTING THE REFRACTORY PERIOD OF THE HEART," and application Ser. No. 11/379,886 by Euler and Burnes entitled, "APPARATUS AND METHODS OF DELIVERING AN ENHANCED REFRACTORY PERIOD STIMULATION THERAPY," the contents of which are fully incorporated by reference herein.

FIELD OF THE INVENTION

The invention relates to cardiac pacing and, more particularly, to delivery of pulse trains of electrical stimulation therapy delivered to multiple sites within a cardiac chamber either during cardiac pacing therapy delivery or passive cardiac monitoring.

BACKGROUND OF THE INVENTION

Refractory period stimulation (RPS) therapy includes therapeutic electrical stimulation that when delivered to myocardial tissue does not trigger or evoke depolarization response from the surrounding myocardial tissue (i.e., does not trigger an electromechanical contraction of the heart). The stimulus does not trigger a mechanical contraction because the stimulus is delivered to the myocardial tissue during a period when the tissue is refractory. Myocardial tissue in an absolute refractory state cannot be captured regardless of the amount of electrical energy delivered thereto while such tissue in a relatively refractory state can be captured provided adequate energy delivery during a given pulse.

The inventor has discovered a particularly efficient RPS therapy delivery regimen that improves ventricular performance for heart failure patients.

SUMMARY

In general, the invention is directed to a medical device, such as an implantable pulse generator (IPG) that delivers stimulation to refractory myocardial tissue. The IPG delivers one or more monophasic stimulation pulses (nominally one to six) to the myocardial tissue during periods when the tissue is absolutely or relatively refractory. Because monophasic stimulation therapy delivery tends to accumulate polarization on the active face of stimulation electrodes, a programmable blanking period of between about 20 ms and about 300 ms is implemented (subsequent to delivery of the last pulse in a RPS pulse train) to allow recovery from the negative effects of such electrode polarization.

In some embodiments, the IPG delivers the pulses during a period from approximately 30 to 200 ms (ms) subsequent to a detected depolarization of myocardial tissue. The stimulation pulses delivered by an IPG according to the invention are on the order of about 0.03 ms to about 1.6 ms with a voltage amplitude of about 0.5 volts to about 8 volts. The amplitude of electrical current of the stimulation pulses is less than or equal to approximately 50 milliamps. According to the invention an IPG delivers the pulses separated by a temporal interval of approximately 10-20 ms (i.e., 50-100 Hz). Furthermore, the pulses are delivered to multiple sites within at least one cardiac chamber—either the left ventricle (LV), right ventricle (RV)—or both ventricles of the heart. In some embodiments, the pulses are applied to the atria as well in order to enhance atrial contractility. In one embodiment, two independent ventricular pacing/sensing medical electrical leads are deployed into communication with a portion of a RV. In another, a multiple electrode epicardial LV lead and a multiple electrode RV lead are deployed into operative communication with stimulation pulse circuitry of an IPG. In the latter embodiment, a bi-ventricular therapy can continue to be delivered (e.g., a cardiac resynchronization therapy, or CRT) with one, all or a subset of the multiple electrodes operatively deployed for RPS therapy delivery. The polarity of RPS may be regulated such that tip of the each lead may serve as a cathode or anode, or the polarity may be alternated by from one train to the next by appropriate programming of the IPG. In one embodiment, each bipolar lead may connected to a separate output channel of an IPG with each channel having independent voltage programming. In another embodiment, multiple leads may be connected in parallel to a single output channel of an IPG.

In some embodiments, an IPG delivers RPS pulses according to a schedule stored in a memory; for example, during certain periods of the day or upon command issued by a clinician or patient. Therapy delivery can be interrupted in the event of relatively high heart rates (relatively short P-P wave or R-R wave intervals) or upon detection of an arrhythmia. In such embodiments, the IPG suspends or withholds delivery of RPS therapy based on detection of such arrhythmias and rapid heart rate (e.g., tachycardia episodes, sinus tachycardia, etc.). Device performance and/or diagnostic information can be stored within a memory structure and reviewed to confirm delivery of a desired therapy regimen (e.g., using a so-called marker channel, or temporal cardiac activity strip and/or a percentage of time, or percentage of cardiac cycles) to track actual therapy delivery.

Thus, one aspect of the invention is to deliver monophasic pulse trains to the ventricles during the refractory period to improve ventricular performance in patients with heart failure.

The details of one or more embodiments of the invention are set forth in the accompanying drawings and the description below. Other features, objects, and advantages of the invention will be apparent from the description and drawings, and from the claims.

DETAILED DESCRIPTION OF THE ILLUSTRATED EMBODIMENTS

In the following detailed description, references are made to illustrative embodiments for an efficient form of RPS therapy delivery including methods and apparatus for practicing same.

The present invention provides enhanced and efficient delivery of monophasic stimulation pulses during the refractory period whether delivered via a unipolar or a bipolar electrode configuration to multiple sites within at least one cardiac chamber. The invention can be practiced in conjunction with or in the absence of diverse cardiac pacing modes via a dedicated lead and/or set of electrodes or using the cardiac pacing electrode configuration of an implanted IPG.

Figure 1:
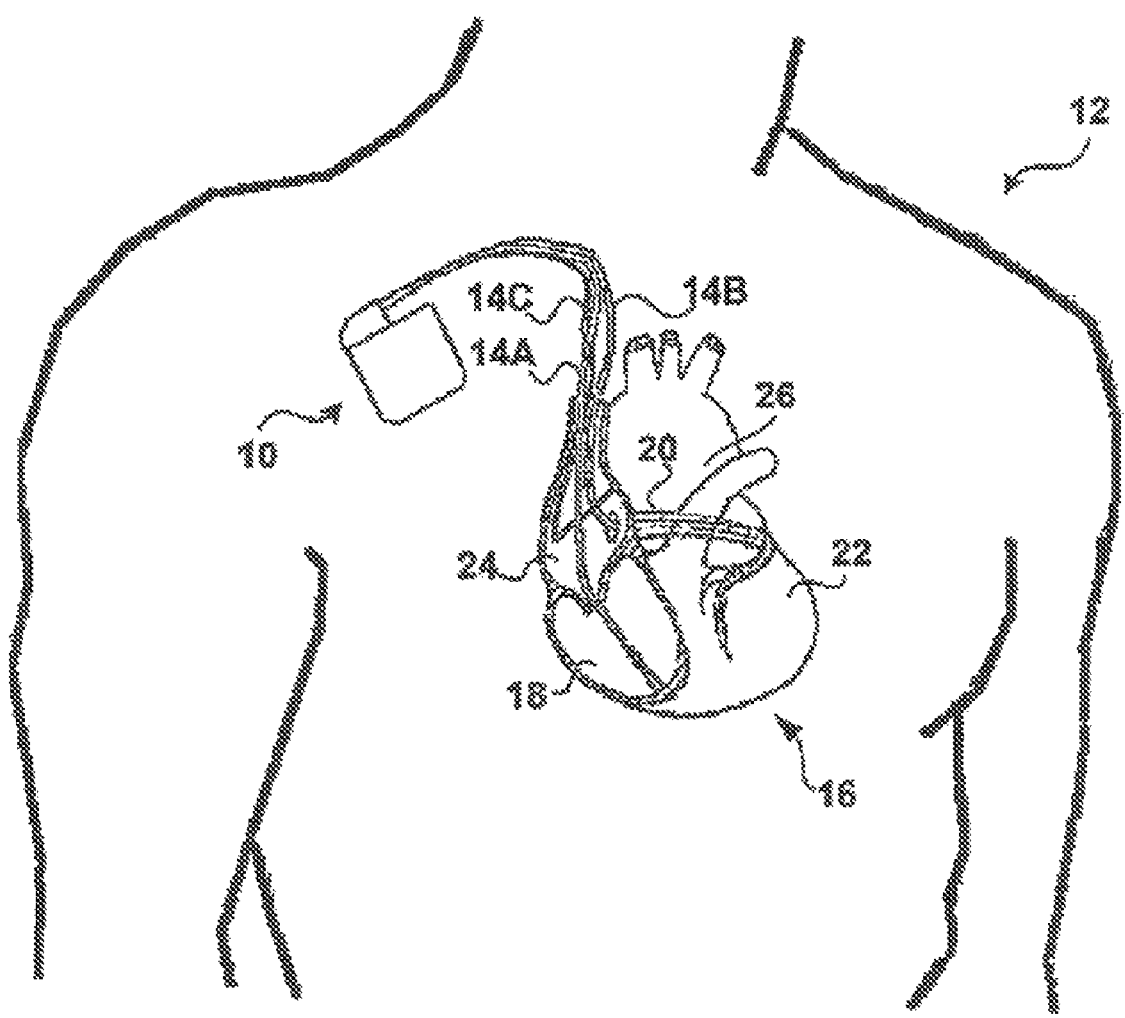
FIG. 1 is a conceptual diagram illustrating an exemplary IPG that delivers RPS pulses according to the invention implanted in a patient.

FIG. 1 is a conceptual diagram illustrating an exemplary implantable pulse generator (IPG) 10 that delivers RPS pulse therapy to myocardial tissue according to the invention. In some embodiments, IPG 10 takes the form of a multi-chamber cardiac pacemaker. In the exemplary embodiment illustrated in FIG. 1, IPG 10 is implanted in a patient 12, and is coupled to leads 14A, 14B and 14C (collectively "leads 14") that extend into the heart 16 of patient 12.

More particularly, RV lead 14A extends through one or more veins (not shown), the superior vena cava (not shown), and right atrium 24, and into RV 18. A LV (coronary sinus) lead 14B extends through the veins, the vena cava, right atrium 24, and into the coronary sinus 20 to a point adjacent to the free wall of LV 22 of heart 16. Right atrial (RA) lead 14C extends through the veins and vena cava, and into the right atrium 24 of heart 16.

Each of leads 14 includes electrodes (not shown), which IPG 10 uses to sense electrical signals attendant to the depolarization and repolarization of heart 16. The IPG 10 delivers RPS pulses to tissue of heart 16 at one or more locations via the electrodes located on one or more of leads 14. In some embodiments, IPG 10 also uses the electrodes located on one or more of leads 14 to deliver pacing pulses to heart 16 (i.e., delivers pulses intended to cause a depolarization and contraction of heart 16). For example, the illustrated multi-chamber IPG 10 can deliver pacing pulses to ventricles 18 and 22 via the electrodes located on leads 14A and 14B with an inter-ventricular delay therebetween to provide cardiac resynchronization therapy (CRT) to heart 16. The electrodes located on leads 14 are unipolar or bipolar, as is well known in the art.

IPG 10 delivers one or more RPS pulses to myocardial tissue of heart 16 during a period in which the tissue is refractory (e.g., when stimulation energy will not trigger tissue depolarization). In some embodiments the energy level of RPS pulses delivered by IPG 10 is similar to that of pacing pulses. In such embodiments, delivery of RPS pulses by IPG 10 does not significantly drain the battery (not shown) of IPG 10, and is unlikely to cause patient 12 to experience pain.

The configuration of IPG 10 and leads 14 illustrated in FIG. 1 is merely illustrative. In various embodiments, IPG 10 can couple to any number of leads 14 that extend to a variety of positions within, on or outside of heart 16. For example, in some embodiments, IPG 10 is coupled to a lead 14 that extends to left atrium 26 of heart 16, or epicardial leads 14 that extend to any position on an exterior surface of heart 16. Consequently, in various embodiments, IPG 10 is capable of delivering RPS pulses to myocardial tissue at any location within or outside of heart 16 via electrodes located on leads 14. Further, IPGs that deliver RPS pulses according to some embodiments of the invention are not implanted in patient 12, but instead are coupled to subcutaneous leads 14 that extend through the skin of patient 12 to a variety of positions within or outside of heart 16.

Figure 2:
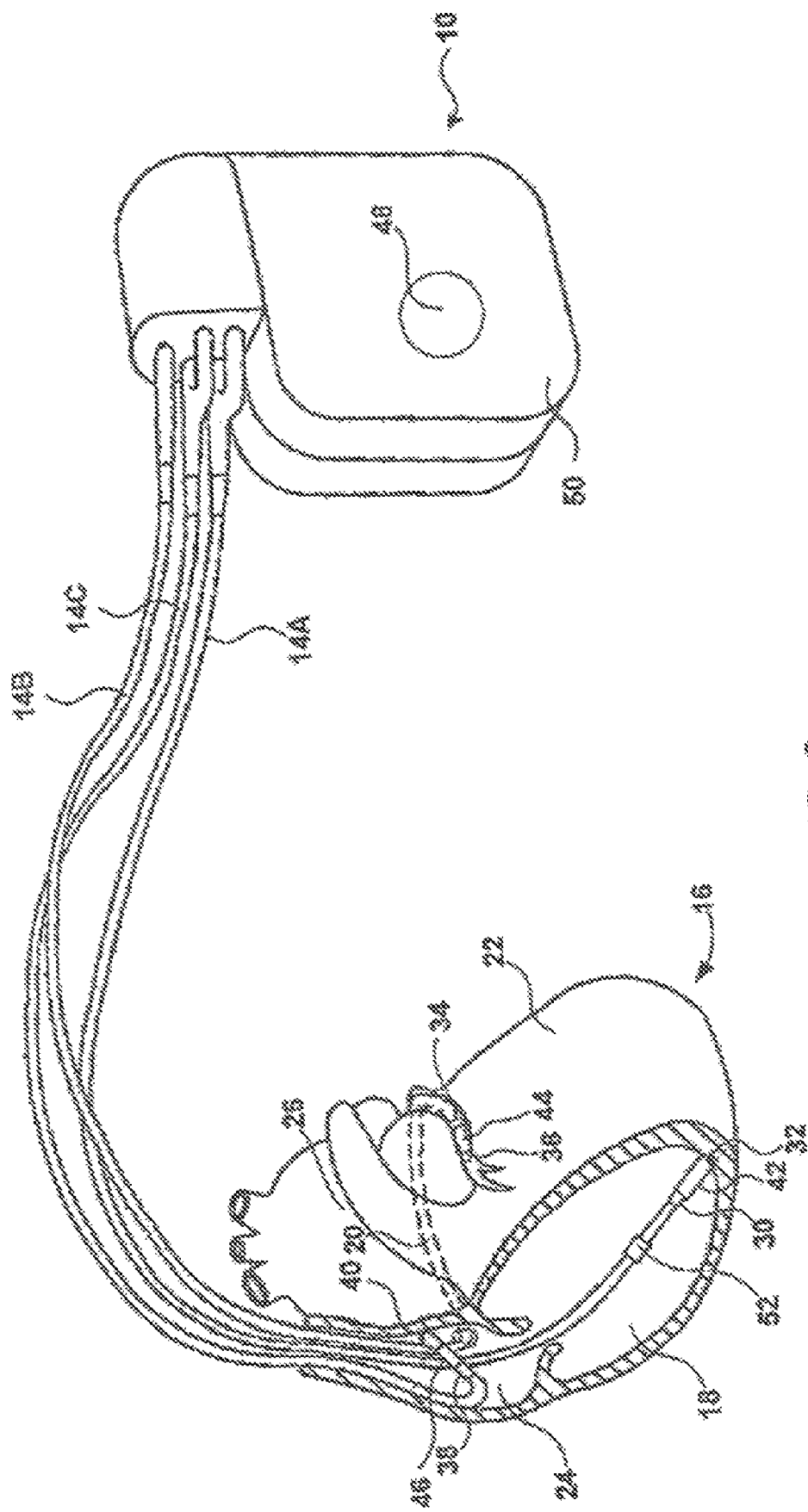
FIG. 2 is conceptual diagram further illustrating the IPG of FIG. 1 and the heart of the patient.

FIG. 2 is a conceptual diagram further illustrating IPG 10 and heart 16 of patient 12. In some embodiments, each of leads 14 includes an elongated insulative lead body carrying a number of concentric coiled conductors separated from one another by tubular insulative sheaths. In the illustrated embodiment, bipolar electrodes 30/32, 34/36, 38/40 are located adjacent distal end of the leads 14A, 14B, 14C, respectively. In exemplary embodiments, electrodes 30, 34 and 38 may take the form of ring electrodes, and electrodes 32, 36, 40 take the form of extendable helix tip electrodes mounted retractably within insulative electrode heads 42, 44, 46, respectively. Each of the electrodes 30-40 is coupled to one of the coiled conductors within the lead body of its associated lead 14.

Sense/pace electrodes 30, 32, 34, 36, 38, 40 sense electrical signals attendant to the depolarization and repolarization of heart 16. The electrical signals are conducted to IPG 10 via leads 14. In some embodiments, as described above, IPG 10 delivers pacing pulses via one or more of the bipolar electrode pairs. In the illustrated embodiment, IPG 10 also includes an indifferent housing electrode 48, formed integrally with an outer surface of the hermetically sealed housing 50 of IPG 10. In such embodiments, IPG 10 is capable of using any of electrodes 30, 32, 34, 36, 38 and 40 for unipolar sensing or pacing in combination with housing electrode 48.

IPG 10 is capable of delivering RPS pulses via any combination of electrodes 30-40 and 48. In some embodiments, IPG 10 delivers defibrillation and/or cardioversion shocks to heart 16 via elongated coil defibrillation electrodes (not shown) carried on one or more of leads 14. In such embodiments, IPG is also capable of delivering RPS pulses via any of electrodes 30-40 in combination with one or more of these defibrillation electrodes.

In some embodiments, IPG 10 includes a sensor 52 that generates a signal as a function of a physiological parameter of patient 12, and delivers RPS pulses to tissue of heart 16 as a function of the physiological parameter. In exemplary embodiments, sensor 52 generates a signal as a function of a physiological parameter that reflects heart rate and/or the presence or absence of an arrhythmia, and IPG 10 monitors the signal to identify a need to inhibit RPS therapy delivery. In response to such a signal, IPG 10 halts delivery of RPS pulses. In the embodiment illustrated in FIG. 2, sensor 52 comprises an electrode pair for sensing heart rate and/or classifying arrhythmia episodes. Thus, sensor 52 could simply comprise a dedicated pair of electrodes or could in fact constitute a pair of pacing/sensing electrodes that were previously deployed for RPS therapy delivery.

Figure 3:
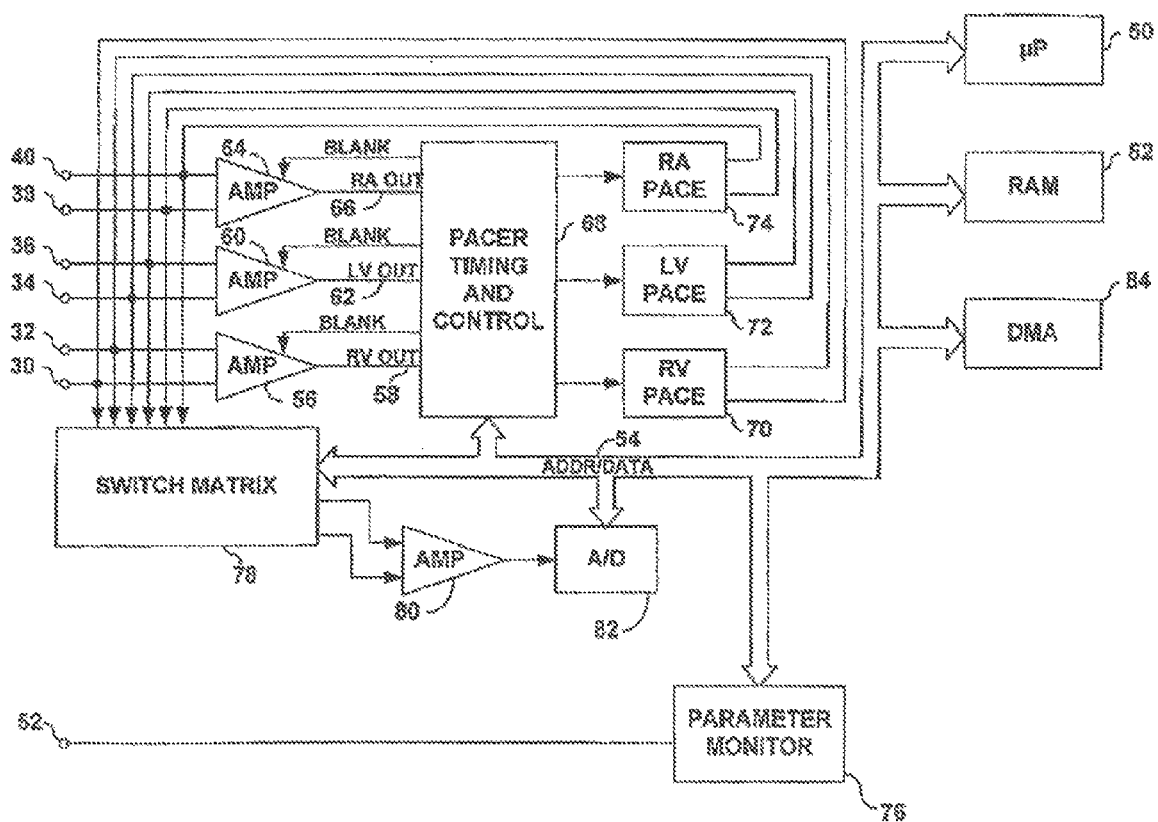
FIG. 3 is a functional block diagram of the IPG of FIG. 1.

FIG. 3 is a functional block diagram of IPG 10. In the illustrated embodiment, IPG 10 takes the form of a multi-chamber pacemaker having a microprocessor-based architecture. However, this diagram should be taken as exemplary of the type of device in which various embodiments of the present invention may be embodied, and not as limiting, as it is believed that the invention may be practiced in a wide variety of device implementations, including devices that are configured to only deliver RPS therapy, but do not provide cardiac pacing, cardioversion, and/or defibrillation therapies. Such an embodiment can include an IPG that merely monitors electrical cardiac activity and titrates RPS therapy delivery.

IPG 10 includes a microprocessor 50 configured to execute program instructions stored in a memory, e.g., a computer-readable medium, such as a ROM, EEPROM, flash memory, RAM 52, DRAM, and the like. Program instructions stored in a computer-readable medium and executed by the microprocessor 50 causes microprocessor 50 to perform the therapy delivery and interruption functions of the present invention. Microprocessor 50 couples to various other components of IPG 10 via an address/data bus 54 as is known in the art.

IPG 10 senses electrical activity within heart 16 via electrodes 30, 32 that are in turn coupled to amplifier 56, which can comprise an automatic gain controlled (AGC) amplifier providing an adjustable sensing threshold as a function of the measured R-wave amplitude. A signal is generated on RV out line 58 whenever the signal sensed between electrodes 30,32 exceeds the present sensing threshold. Thus, electrodes 30, 32 and amplifier 56 are used to detect evoked and intrinsic RV depolarizations.

Electrodes 34, 36 are coupled to amplifier 60, which also takes the form of an AGC amplifier providing an adjustable sensing threshold as a function of measured R-wave amplitude. A signal is generated on LV out line 62 whenever the signal sensed between electrodes 34, 36 exceeds the present sensing threshold. Thus, electrodes 34, 36 and amplifier 60 are used to detect evoked and intrinsic LV depolarizations.

Electrodes 38, 40 are coupled to amplifier 64, which takes the form of an AGC amplifier providing an adjustable sensing threshold as a function of the measured P-wave amplitude. A signal is generated on RA out line 66 whenever the signal between electrodes 38, 40 exceeds the present sensing threshold. Thus, electrodes 38, 40 and amplifier 64 are used to detect evoked and intrinsic atrial depolarizations.

IPG 10 delivers RPS pulses to tissue of heart 16. Pacer timing/control circuitry 68 controls delivery of RPS pulses by one or more of output circuits 70-74 via electrodes 3040. Output circuits 70-74 include known circuitry for storage and delivery of energy in the form of pulses, such as switches, capacitors, and the like.

Pacer/timing and control circuitry 68 includes programmable digital counters that control the timing of delivery of RPS pulses. Pacer/timing control circuitry 68 further controls the width and amplitude of RPS pulses delivered by output circuits 70-74. Circuitry 68 controls the timing, width and amplitude of RPS pulses delivered by output circuits 70-74 based on information received from microprocessor 50 via data bus 54. The timing, width and amplitude of RPS pulses delivered by IPG 10 according to the invention will be described in greater detail below.

Microprocessor 50 controls the delivery of RPS pulses by IPG 10 by indicating to pacer/timing control circuitry 68 when RPS pulses are to be delivered, via which of electrodes 30-40 and 48 RPS pulses are to be delivered, and the timing, width and amplitude of RPS pulses to be delivered. In some embodiments, microprocessor 50 controls delivery of RPS pulses such that RPS therapy delivery occurs on a diurnal basis, upon patient activation, and/or for a preset duration. In some embodiments, microprocessor 50 enables delivery of RPS pulses according to a schedule stored in a memory, such as RAM 52, which indicates times of day or the like for delivery of RPS pulses.

In some embodiments, microprocessor 50 controls delivery of RPS pulses as a function of a physiological heart rate or presence of an arrhythmia condition parameter of a patient 12, as discussed above.

Although described herein in the context of a microprocessor-based pacemaker embodiment IPG 10, the invention may be embodied in various IPGs that include one or more processors, which may be microprocessors, DSPs, FPGAs, or other digital logic circuits. Further, in some embodiments, IPG 10 does not digitally process the electrogram signal to detect ischemia. For example, IPG 10 may include analog slope or threshold detecting amplifier circuits to identify and measure the QT interval and/or ST segment within an electrogram signal, as is known in the art.

In some embodiments, IPG 10 paces heart 16. Pacer timing/control circuitry 78 includes programmable digital counters which control the basic time intervals associated with modes of pacing. Circuitry 78 also preferably controls escape intervals associated with pacing. For example, where IPG 10 paces right atrium 24, timing/control circuitry 78 triggers generation of pacing pulses by pacer output circuit 84, which is coupled to electrodes 38, 40, upon expiration of an atrial escape interval.

IPG 10 can be configured to delivery bi-ventricular pacing therapy such as a CRT therapy. When delivering CRT, pacer timing/control circuitry 68 triggers generation of pacing pulses for one of ventricles 18 ,20 by the respective one of pacer output circuits 70, 72 upon expiration of an A-V escape interval, and the other of ventricles 18, 20 by the respective one of pacer output circuits 70, 72 upon expiration of a V-V escape interval.

Pacer timing/control circuitry 68 resets escape interval counters upon detection of R-waves or P-waves, or generation of pacing pulses, and thereby controls the basic timing of cardiac pacing functions. Intervals defined by pacing circuitry 68 also include refractory periods during which sensed R-waves and P-waves are ineffective to restart timing of escape intervals, and the pulse widths of the pacing pulses. The durations of these intervals are determined by microprocessor 50 in response to data stored in RAM 52, and are communicated to circuitry 68 via address/data bus 54. Pacer timing/control circuitry 68 also determines the amplitude of the cardiac pacing pulses under control of microprocessor 50.

Microprocessor 50 operates as an interrupt driven device, and is responsive to interrupts from pacer timing/control circuitry 68 corresponding to the occurrence of sensed P-waves and R-waves and corresponding to the generation of cardiac pacing pulses. Those interrupts are provided via data/address bus 56. Any necessary mathematical calculations to be performed by microprocessor 50 and any updating of the values or intervals controlled by pacer timing/control circuitry 58 take place following such interrupts.

Figure 4:
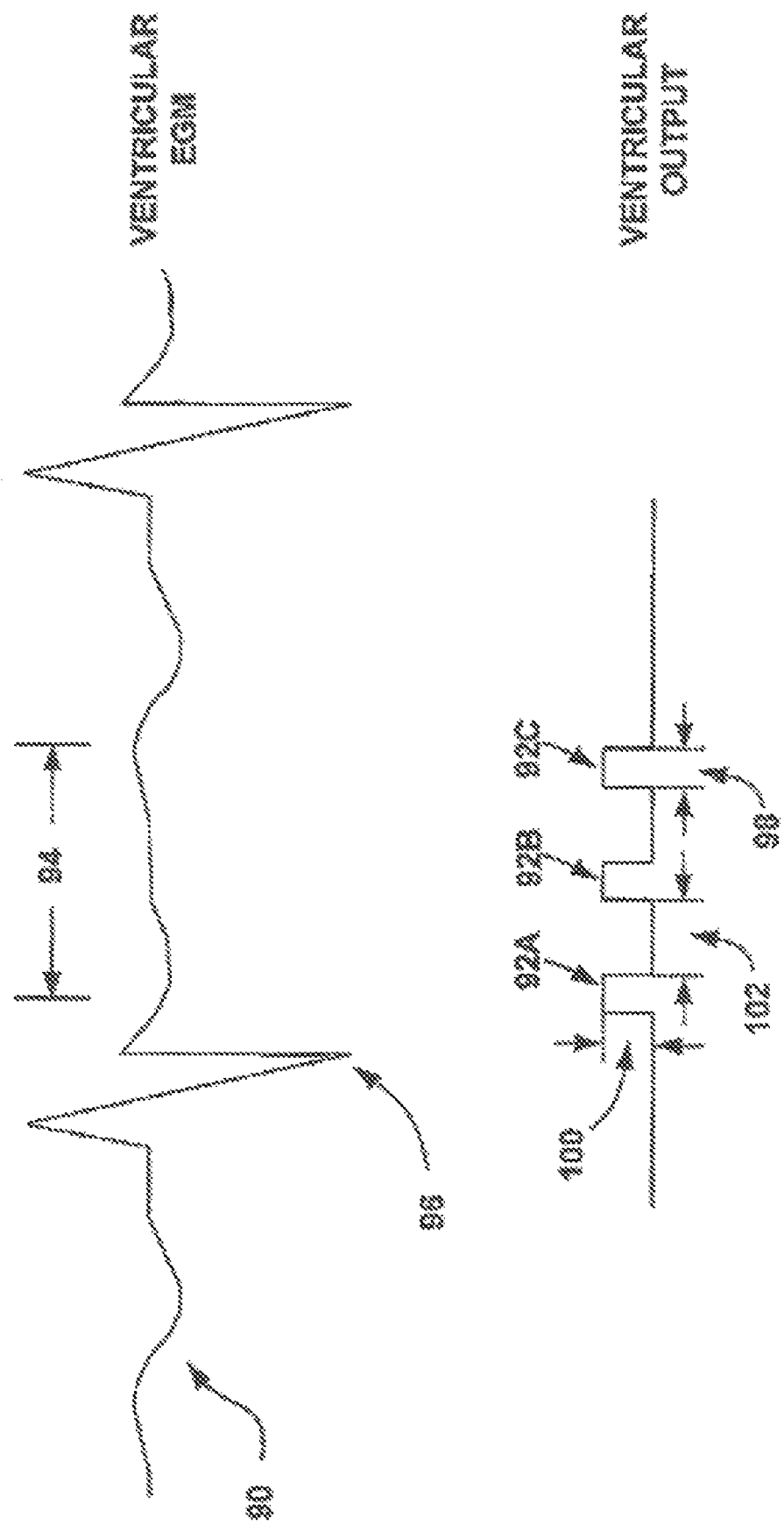
FIG. 4 is a timing diagram illustrating an example electrogram and exemplary RPS pulses.

FIG. 4 is a timing diagram illustrating an example electrogram signal 90 and exemplary RPS pulses 92A-C (collectively "RPS pulses 92") delivered by IPG 10 according to an embodiment of the invention. In the illustrated example, electrogram signal 90 is a ventricular electrogram signal, e.g., a signal detected via one of leads 14A and 14B. Further, as illustrated in FIG. 4, RPS pulses 92 are delivered to one of ventricles 18, 22 via one of leads 14A, 14B.

IPG 10 delivers RPS pulses 92 to tissue in heart 16 during a period 94 when the tissue is refractory. When directed to control delivery of RPS pulses by microprocessor 50, pacer timing/control circuitry 68 detects occurrence of an R-wave 96 in the manner described above with reference to FIG. 3, and delivers RPS pulses during period 94 subsequent to R-wave 96 when tissue is refractory. In exemplary embodiments, circuitry 68 controls delivery of RPS pulses during a period 94 that extends from forty to eighty ms after detection of R-wave 96 to ensure that the tissue is refractory and that RPS pulses 92 are delivered prior to a second depolarization of the tissue. Where RPS pulses 92 are delivered to tissue of one of atria 24, 26, refractory period 94 may be determined based on detection of a P-wave by circuitry 68 in the manner described above.

As indicated above, in exemplary embodiments the energy level of a pulse 92 of the pulse train consists of about: a pulse width of about 0.03 ms to about 1.6 ms; a current amplitude 100 of each pulse 92 is less than or equal to approximately twenty milliamps; a voltage amplitude is between about 0.5 volts and about 8 volts; and the pulse train is delivered between about 50 Hz and 100 Hz (i.e., 10-20 ms separation between pulses).

Although illustrated as having the same width 98 and amplitude 100, pacer timing/control circuitry 68 can deliver each of pulses 92 with different widths 98 and amplitudes 100.

Pacer timing/control circuitry 68 controls delivery of one or more RPS pulses 92 during refractory period 94 including a programmable blanking period of about 50 ms and 300 ms following delivery of the last pulse in a given pulse train. The blanking period allows the electrodes to recover from polarization effects following delivery of a pulse train. A pulse train begins to be delivered from about 30 ms to about 200 ms following detection of a paced or intrinsic depolarization.

In the example illustrated in FIG. 4, circuitry 68 controls delivery of a train of three pulses 92A-C during refractory period 94. In exemplary embodiments, circuitry 68 controls delivery of pulse trains that include six of fewer RPS pulses 92 during refractory period 94.

Circuitry 68 controls delivery of pulses 92 such that they are separated by an interval 102. In exemplary embodiments, interval 102 is less than or equal to about 20 ms (50 Hz). Although illustrated as separated by a constant interval 102, in some embodiments, pulses 92 are separated by intervals 102 that vary from pulse-to-pulse and/or from pulse train to pulse train.

In accordance with an aspect of the present invention, methods and apparatus are provided efficient, programmable methods and apparatus for delivering a RPS therapy to one or more chambers of a heart. Single chamber and multiple chamber embodiments of the invention include endocardial and epicardial electrodes locations and permit the continued simultaneous delivery of a CRT or other pacing regimen. Diagnostics included within the context of the invention include arrhythmia detection algorithms that, upon confirmation of an arrthymia episode, interrupt RPS therapy delivery and provide temporal records of actual therapy delivery (percentage time, percentage cardiac cycles, etc.). In addition, RPS therapy delivery will be interrupted according to the invention in the event that a relatively high heart rate is detected.

In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

The invention claimed is:

1. A method of delivering a refractory period stimulation (RPS) therapy, comprising:

delivering between one and six successive monophasic cardiac stimulation pulses to multiple sites within a single cardiac chamber during a refractory period of the cardiac chamber, wherein said successive pulses are separated by approximately 10 and about 20 milliseconds (ms), wherein each said pulse has a pulse duration of between 0.03 ms and 1.6 ms and wherein each said pulse has a voltage amplitude of between 0.5 volts and 8.0 volts; and interrupting delivery of the monophasic cardiac stimulation pulses in the event that one of a supra-threshold heart rate is detected and an arrhythmia condition is detected.

2. A method according to claim 1, wherein the single cardiac chamber comprises a ventricular chamber.

3. A method according to claim 2, wherein the multiple sites comprise multiple endocardial sites.

4. A method according to claim 1, wherein the pulses are delivered to the multiple sites in communication with the left ventricle (LV) and right ventricle (RV).

5. A method according to claim 4, wherein the multiple site of the RV comprise endocardial sites and the multiple site of the LV comprise epicardial sites.

6. A method according to claim 5, wherein the epicardial comprises at least two locations within a portion of one of a great cardiac vein and a lateral cardiac vein.

7. A non-transitory computer readable medium for executing instructions to deliver a refractory period stimulation (RPS) therapy, comprising:

instructions for delivering between one and six successive monophasic cardiac stimulation pulses to multiple sites within a single cardiac chamber during a refractory period of the cardiac chamber, wherein said successive pulses are separated by approximately 10 to about 20 milliseconds (ms), wherein each said pulse has a pulse duration of between 0.03 ms and 1.6 ms, and wherein each said pulse has a voltage amplitude of between 0.5 volts and 8.0 volts; and instructions for interrupting delivery of the monophasic cardiac stimulation pulses in the event that one of a supra-threshold heart rate is detected and an arrhythmia condition is detected.

8. A medium according to claim 7, wherein the single cardiac chamber comprises a ventricular chamber.

\* \* \* \* \*